United States Patent [19]

Goodson et al.

[11] 4,117,714
[45] Oct. 3, 1978

[54] METHOD AND APPARATUS FOR CONTINUOUSLY EXTRACTING TRACE CONTAMINANTS FROM AIR AND MONITORING THE CONTAMINANT CONTENT THEREOF

[75] Inventors: Louis H. Goodson, Kansas City; William B. Jacobs, Independence, both of Mo.

[73] Assignee: Midwest Research Institute, Kansas City, Mo.

[21] Appl. No.: 796,160

[22] Filed: May 12, 1977

[51] Int. Cl.² .............................................. G01N 31/00
[52] U.S. Cl. .............................................. 73/23; 55/18; 55/89; 55/92; 55/95; 55/229; 55/238; 55/241; 55/270; 261/79 A; 73/421.5 R; 73/28; 23/232 R; 422/88
[58] Field of Search ............... 55/89, 92, 95, 223, 55/229, 235–238, 241, 248, 257 R, 270, 18; 261/79 A; 73/28, 421.5 R, 421.5 A, 23 R; 23/232 R, 254 R

[56] References Cited

U.S. PATENT DOCUMENTS

| 3,397,514 | 8/1968 | Rothfeld et al. | 55/248 |
|---|---|---|---|
| 3,488,924 | 1/1970 | Reeve | 55/89 |
| 3,546,851 | 12/1970 | Hardison et al. | 55/238 |
| 3,566,582 | 3/1971 | Yankura | 55/92 |
| 3,641,821 | 2/1972 | Junker et al. | 73/421.5 R |
| 3,651,619 | 3/1972 | Miura | 55/237 |
| 3,667,191 | 6/1972 | Prince et al. | 55/89 |
| 3,668,825 | 6/1972 | McIlvaine | 55/229 |
| 3,944,402 | 3/1976 | Cheremisinoff | 55/92 |

*Primary Examiner*—Frank W. Lutter
*Assistant Examiner*—David L. Lacey
*Attorney, Agent, or Firm*—D. A. N. Chase

[57] ABSTRACT

Air that is desired to be examined for impurities is drawn through a concentrator comprising a cylindrical receptacle into which the air is introduced at the base portion of the receptacle in a direction tangentially of the cylindrical wall. A scrubbing liquid such as water is supplied to the receptacle and withdrawn therefrom on a continuous basis. The quantity of water only partially fills the region at the base of the receptacle where the air is tangentially introduced, with the result that the water is caused to rotate vigorously within the cylindrical wall as a thin film. The air is initially beneath the rotating film but then passes upwardly through it and is efficiently scrubbed. Gaseous and particulate impurities in the air are thus extracted into the water, and the same is drained from the receptacle and monitored for contaminant content.

8 Claims, 7 Drawing Figures

U.S. Patent  Oct. 3, 1978  Sheet 1 of 2  4,117,714
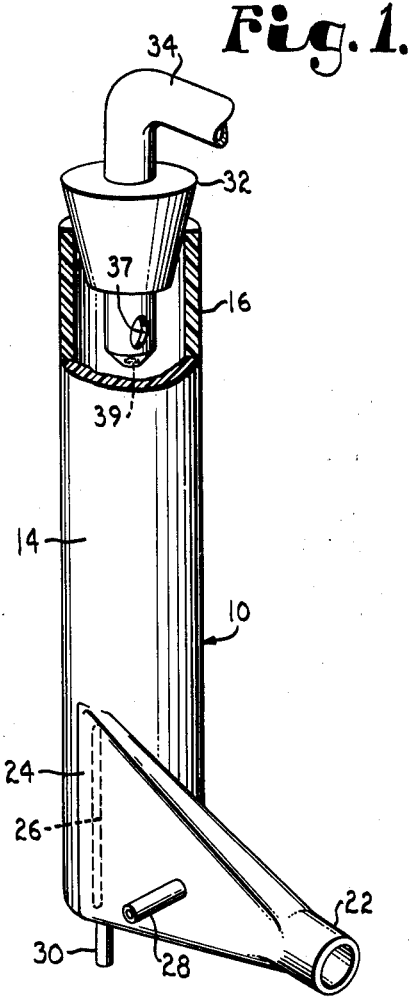
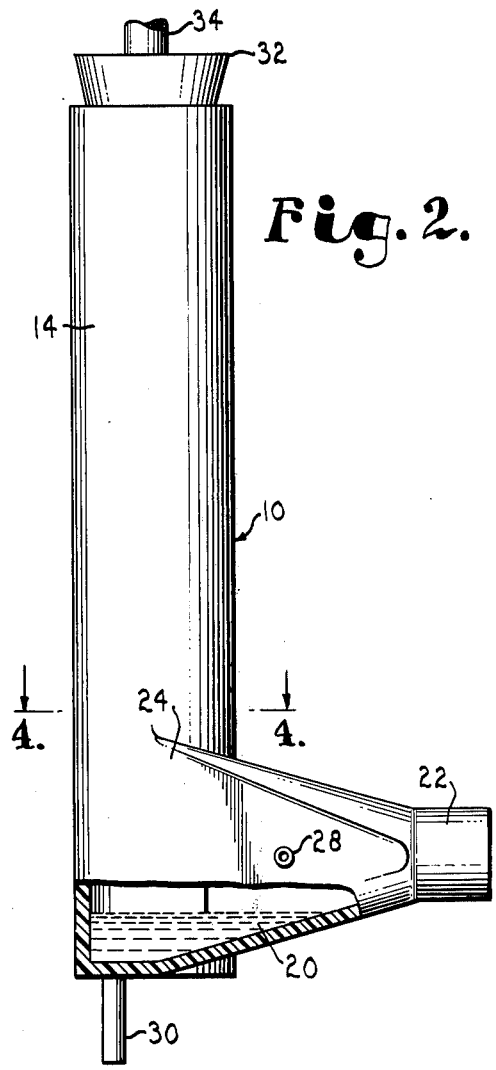
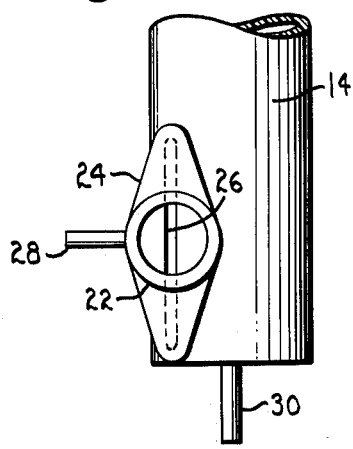
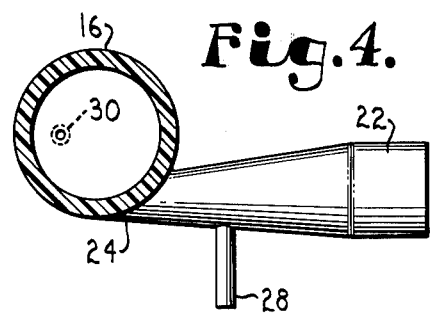

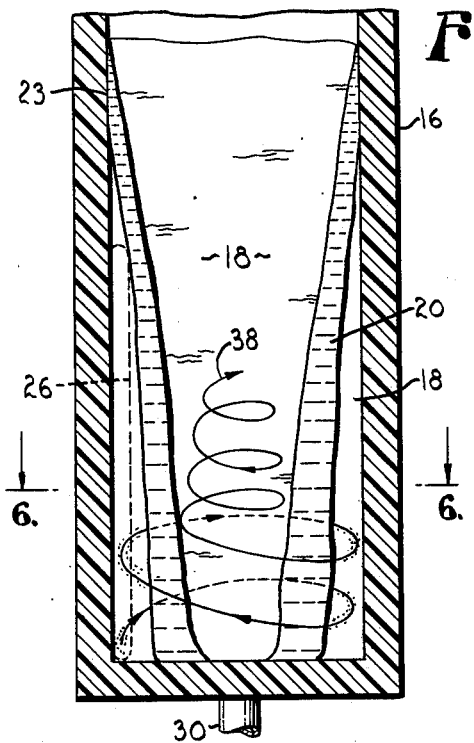
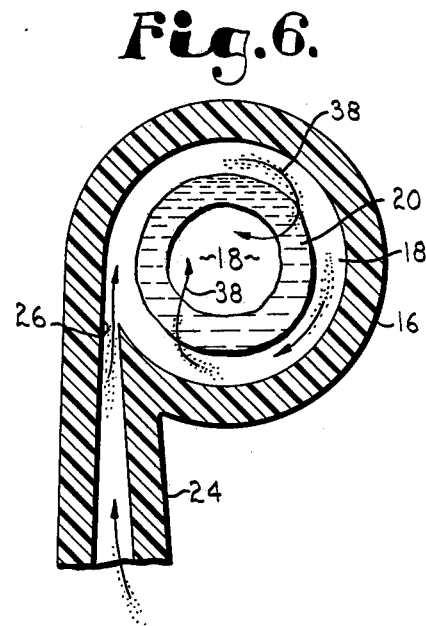
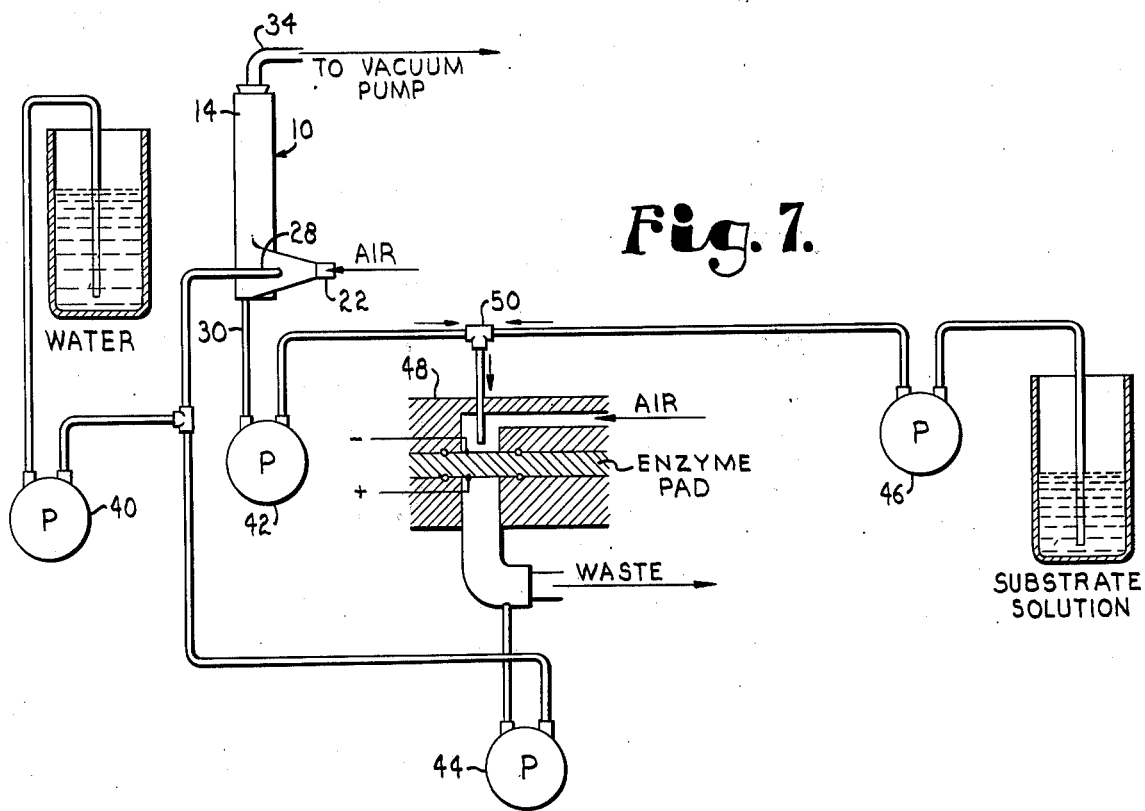

METHOD AND APPARATUS FOR CONTINUOUSLY EXTRACTING TRACE CONTAMINANTS FROM AIR AND MONITORING THE CONTAMINANT CONTENT THEREOF

This invention relates to improvements in the detection of impurities in air or other gases and, in particular, to an improved method and apparatus for concentrating trace quantities of impurities so that they may be monitored on a real time basis.

In laboratories, manufacturing facilities and warehouses where gases or other types of impurities could be accidentally released into the air in harmful amounts, it is important to provide an air monitoring system which will detect such impurities before they reach a harmful level. Under current detection techniques, it is required that the contaminants in the air first be concentrated before a successful analysis can be made. Previous methods of concentrating trace quantities of impurities in air have employed dry adsorbents, liquid bubblers or impingers, but in these methods batchwise extraction of soluble pollutants from air is successful only so long as the air flow rates are kept relatively low. Efficiencies decrease markedly as air flow rates through such concentrators are increased. Since efficient extraction of impurities from large volumes of air into a small volume of liquid is necessary to achieve high sensitivity in the detection and monitoring of air pollutants, these prior methods present serious disadvantages of both lowered extraction efficiency and ability to extract the impurities on a continuous basis.

It is, therefore, an important object of the present invention to provide a method and apparatus for effectively and efficiently extracting impurities from air or other gases, and which are not subject to the disadvantages discussed above.

More specifically, it is an important object of this invention to provide a method and apparatus as aforesaid for effectively and efficiently extracting and concentrating trace quantities of impurities from air at relatively high air flow rates.

Another important object of this invention is to provide a method and apparatus as aforesaid which extracts the impurities on a continuous basis rather than through batchwise extraction.

Still another important object of the invention is to provide a method and apparatus as aforesaid which permits impurities in air or other gases to be collected and analyzed or monitored on a real time basis.

Still another important object of the invention is to provide a method and apparatus for extracting impurities from a gas, wherein the extraction of the impurities is accomplished by passing the gas through a thin film of scrubbing liquid.

Yet another important object of the invention is to provide a method and apparatus as aforesaid for the extraction of impurities with a thin film of scrubbing liquid, wherein the thin film is produced in a simple concentrator device by the introduction of air or gas flow into the concentrator in a manner to spin the scrubbing liquid and thereby form a film thereof.

Furthermore, it is an important object of this invention to provide such a method and apparatus where the scrubbing liquid is supplied and withdrawn continuously so that the impurities in the gas stream may be monitored on a real time basis.

DESCRIPTION OF THE DRAWINGS

FIG. 1 is a perspective view of a concentrator employing the present invention;

FIG. 2 is a side elevational view of the concentrator of FIG. 1 with the bottom part of the flared tube and cylindrical wall of the receptacle broken away to reveal the scrubbing liquid at rest before air flow;

FIG. 3 is a fragmentary detail view of the bottom part of the concentrator illustrating the manner in which the flared end of the air tube is tangentially connected to a slit in the wall of the cylindrical receptacle;

FIG. 4 is a horizontal sectional view taken along line 4—4 of FIG. 2;

FIG. 5 is an exaggerated side detail view of the bottom part of the receptacle when both the air and scrubbing liquid are flowing therethrough;

FIG. 6 is a horizontal sectional view taken along line 6—6 of FIG. 5; and

FIG. 7 is a diagrammatic illustration of the concentrator and associated components shown as part of an air monitoring system.

DETAILED DESCRIPTION

The concentrator 10 embodying the improvements of the present invention is shown in detail in FIGS. 1 through 6 and diagrammatically as part of a complete air monitoring system in FIG. 7.

Referring to FIGS. 1-6, the concentrator 10 includes a cylindrical receptacle 14 having a cylindrical wall 16, the receptacle 14 receiving the desired-to-be examined air or other gas 18 and a scrubbing liquid (such as water) 20. An air tube 22 is provided with a flared end 24 joined to the bottom portion of the receptacle 14 in registration with an elongated, vertical slit or inlet 26 in the cylindrical wall 16. A liquid inlet consisting of a small tube 28 connected to the middle of the flared end portion of the air tube 22 is provided for introducing the scrubbing liquid 20 into the receptacle 14. Accordingly, both the liquid inlet 28 and the air tube 22 are in communication with the receptacle 14 via the slit 26.

The receptacle 14 has closed ends and at its bottom a liquid outlet or drain 30 is provided for withdrawing the liquid on a continuous basis. A suitable stopper 32 is provided to cap the receptacle 14, and inserted in the stopper 32 is an air outlet tube 34 which communicates with the receptacle above the region of the cylinder where the air (or other gas) and the liquid are in contact with one another. The end of air outlet tube 34 within receptacle 14 presents a spray trap having diametrically opposed, circular air entrance openings 37 in the sidewall of tube 34. Below the aligned openings the tube 34 is uniformly tapered to a small circular opening 39 at its tip. The exact placement of the air outlet and the liquid inlet is not critical; for example, the liquid inlet could be located in the cylindrical wall 16 of the receptacle 14 near its top.

In FIG. 7 an air monitoring system is partially illustrated and, in addition to the concentrator 10, includes four pumps 40, 42, 44 and 46 and an enzyme pad sensor unit 48. The pump 40 in operation pumps fresh water from a suitable source as illustrated to the liquid inlet 28 of the concentrator, and pump 42 withdraws the water from outlet 30 and pumps the same to the sensor unit 48. The pump 44 is used when it is desired to recirculate the sampling liquid to increase system sensitivity. Pump 46 is employed to pump substrate solution to the enzyme pad via a tee 50. A suitable vacuum pump (not shown)

has its intake connected to the air outlet tube 34 of the concentrator 10, thereby drawing the air to be examined into the concentrator through the air inlet tube 22. It should be understood that the air tube 22 is in communication with the air space to be monitored for the possible presence of contaminants.

OPERATION

As is especially evident in FIG. 6, the flared end 24 of the air tube 22 merges with the cylindrical wall 16 in a manner such that the air introduced into the cylinder enters the same in a tangential direction. As seen in FIG. 2, the water 20 does not fill the region at the base of the receptacle 14 defined by the flared end 24 but, unstead, fills such region to approximately one-fourth if its capacity. FIG. 2 shows the water 20 at rest before introduction of the air stream into the receptacle.

When the air is injected into the cylinder from the tangentially connected tube 22 by the pressure differential created by operation of the vacuum pump (discussed above with reference to FIG. 7), the tangentially introduced air rotates or spins the water 20 as a thin scrubbing film as shown in FIG. 5. The thickness of the film 20 is exaggerated in FIG. 5 for clarity. It may be seen that the air 18 upon entering the cylinder is between the cylindrical wall 16 and the rotating film 20, and that an annhlar sear 23 is formed above the vertical slit 26 by the upper end portion of the rotating film 20. This seal 23 against the inner surface of the cylindrical wall 16 prevents upward passage of the air stream along the cylindrical inner surface. Therefore, the air rotates or swirls around the cylindrical wall 16 and is forced to progress inwardly through the thin film as illustrated by the arrows 38. After passing through the film of water, the air is still rotating and is drawn upwardly through the receptacle 14 in a spiral path to the outlet tube 34 and the intake of the vacuum pump, and is further scrubbed as the air spirals upwardly since the air continues to impinge on the water film. Accordingly, the air 18 is scrubbed as it passes through and above the rotating film 20 and any impurities therein are dissolved or entrapped in the water film.

The air 18 as it spirals upwardly as illustrated by arrows 38 in FIG. 5 enters air outlet tube 34 through the entrance openings 37. The air 18 has to undergo substantially a right angle bend to pass into the air outlet tube and out of the receptacle 14. Accordingly, any liquid particles entrained in the air (thus forming an aerosol) after passing through the film 20 will tend to impinge and collect on the inner surfaces of the tube 34 and drip from the small circular opening 39. Thus, the liquid 20 is prevented from leaving the cylinder via the air outlet tube 34.

While the air is being continuously drawn through the receptacle 14, the water 20 is likewise being constantly supplied to the receptacle and drained or pumped therefrom at approximately the same rate. Accordingly, the scrubbing liquid is resupplied on a continuous basis to permit constant monitoring of the presence of gaseous and particulate impurities. This in conjunction with the extraction of the impurities by a relatively small quantity of scrubbing liquid (the thin water film) enables the concentrator of the present invention to continuously concentrate impurities from a stream of air into a small stream of liquid.

Referring to FIG. 7, in the air monitoring system shown the air is sampled continuously even though the water is examined in batches. The water is provided for examination on a short duration, cyclic bases, successive six-minute cycles being typical. During each cycle, the water is pumped into the concentrator 10 and withdrawn by the pumps 40 and 42, the substrate pump 46 is operated, and constant current is applied to the electrodes of the enzyme pad so that the necessary voltage measurements may be made to determine the presence or nonpresence of inhibitors (impurities in the air). A feature of the present invention is the ability to recirculate the water from the enzyme pad to the concentrator in order to increase the sensitivity of the system by permitting a higher concentration of impurity agents to build up in the sampling liquid. This is accomplished by the recirculating pump 44.

A typical cycle employing the recirculation feature is as follows. It is assumed that the flow rate of pump 40 is 1 ml/min, the flow rate of pump 42 is 5 ml/min, and the flow rate of pump 44 is 4 ml/min. In this case, 5 ml/min of water is pumped through the concentrator 10 and 80 percent of this volume (i.e., 4 ml/min) is recirculated to the concentrator. The pumps are operated for the first 5 minutes of the 6 minute water detection cycle. Then the substrate pump 46 is activated and air is introduced into the sensor unit 48 as illustrated by the arrow, and waste removed as indicated. To complete the cycle, current is applied to the pad electrodes and the necessary measurements are made.

For continuous air flow rates of from 40 to 150 liters per minute, the cylindrical receptacle 14 may typically have a height of approximately 15 cm. and an inside diameter of approximately 25 mm. The length of the vertical slit 26 would be approximately 45 to 50 mm. and the width on the order of 1 mm. The water may be drained and resupplied at throughputs depending upon the particular application, ranging for example from 1 to 5 ml. per minute. An electronic control (not shown) actuated by changes in pressure across the orifice (slit 26) may be utilized to regulate either the input pump or the exit pump (pumps 40 and 42 in FIG. 7) to maintain the proper volume of water in the concentrator at all times. A concentrator of these dimensions would have a fixed volume of water of from 3 to 5 ml. Considerable variation in air and liquid flow rates can be achieved through the use of other dimensions for the various parts of the concentrator.

In summary, some of the important advantages of the concentrator of the present invention include low fabrication and materials cost; high sampling efficiency; adaptability to air flow rates in the range of 20 to 500 liters per minute; small size; small liquid volume necessary for sample collection; suitability for incorporation into automatic monitoring equipment; and suitability for continuous monitoring applications as discussed in detail hereinabove. A specific application of the concentrator is in the extraction of trace contaminants from air in installations where pesticides are being manufactured, handled or stored.

Having thus described the invention, what is claimed as new and desired to be secured by Letters Patent is:

1. A method of extracting impurities from a gas and monitoring the impurity content thereof on a real time basis, said method comprising the steps of:

providing a receptacle having a region defined by a generally cylindrical wall;

continuously supplying a fresh scrubbing liquid to said receptacle which flows to said region;

continuously withdrawing the liquid from said region at substantially the same rate that it is being supplied thereto to maintain a predetermined quantity of scrubbing liquid therein;

introducing said gas under pressure into said region in a direction tangentially of said wall to rotate the liquid therein as a thin film and cause the gas to pass through said film in scrubbing relationship thereto, so that impurities in the gas are extracted into the liquid, and out of said region; and examining at least a portion of the withdrawn liquid to detect impurities therein extracted from the gas.

2. The method as claimed in claim 1, further comprising the step of recirculating a portion of the withdrawn liquid.

3. Apparatus for extracting impurities from a gas and for monitoring the impurity content on a real time basis, said apparatus comprising:

a receptacle having a region provided with a generally cylindrical wall, an inlet in said wall at said region, and a gas outlet communicating with said receptacle, said receptacle containing a scrubbing liquid in said region and having a liquid outlet communicating with said region;

liquid input means for introducing said scrubbing liquid into said receptacle for flow to said region;

means connected to said input means and said liquid outlet for continuously supplying fresh liquid to said region and continuously withdrawing the liquid therefrom to maintain a predetermined quantity of scrubbing liquid therein;

means registering with said inlet for introducing gas under pressure into said region in a direction tangentially of said wall to rotate the liquid therein as a thin film forming a seal with said wall above said inlet, and cause the gas to pass through said film in scrubbing relationship thereto to said outlet, whereby impurities in the gas are extracted into the liquid;

means for detecting impurities in said liquid; and means for flowing at least a portion of said withdrawn liquid to said detecting means to monitor the presence of impurities in the withdrawn liquid extracted from the gas.

4. The apparatus as claimed in claim 3, wherein said receptacle is in an upright position and has a lower portion defining said region, said gas outlet communicating with said receptacle above said region.

5. The apparatus as claimed in claim 3, wherein said liquid supplying and withdrawing means includes means for recirculating a portion of the withdrawn liquid.

6. The apparatus as claimed in claim 3, wherein said cylindrical wall is generally upright and has an upwardly and downwardly extending, elongated slit therein presenting said inlet in the wall, and wherein said gas introducing means includes a tube disposed to direct said gas under pressure through said slit in said direction tangentially of the wall.

7. The apparatus as claimed in claim 6, wherein said liquid at rest only partially fills said region to a level substantially below the top of said slit.

8. The apparatus as claimed in claim 3, wherein said gas outlet includes spray trap means for preventing liquid carried by the gas from exiting the receptacle via the gas outlet.

* * * * *